US00PP37164P2

(12) United States Plant Patent
Ranney et al.

(10) Patent No.: US PP37,164 P2
(45) Date of Patent: Dec. 23, 2025

(54) ***BERBERIS* PLANT NAMED 'NCBX3'**

(50) Latin Name: ***Berberis thunbergii* x *Berberis* x *media***
Varietal Denomination: NCBX3

(71) Applicant: North Carolina Sate University, Raleigh, NC (US)

(72) Inventors: Thomas Green Ranney, Arden, NC (US); Nathan Lynch, Arden, NC (US); John Tyler Nix, Arden, NC (US); Andra Windorf Nus, Arden, NC (US); Irene Palmer, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 19/245,277

(22) Filed: Jun. 21, 2025

(51) Int. Cl.
*A01H 5/00* (2018.01)
*A01H 6/00* (2018.01)

(52) U.S. Cl.
USPC ..... Plt./241
CPC ..... *A01H 6/00* (2018.05)

(58) Field of Classification Search
USPC ..... Plt./241
CPC ..... A01H 5/00
See application file for complete search history.

*Primary Examiner* — Kent L Bell

(57) ABSTRACT

A new and distinct cultivar of *Berberis* plant named 'NCBX3' is disclosed, characterized by dark red, glossy foliage which develops a chartreuse margin with maturity. Bright foliage color persists all season long. Plants have a low, mounding habit and small spines. The new cultivar is a *Berberis*, normally used for outdoor ornamental purposes.

3 Drawing Sheets

Latin name of the genus and species: *Berberis thunbergii* x *Berberis* x *media.*

Cultivar denomination: 'NCBX3'.

BACKGROUND OF THE INVENTION

The new *Berberis* cultivar is a product of a planned breeding program conducted by the inventors to develop cultivars with new foliage colors and forms. The seed parent was the unpatented *Berberis thunbergii* 'Concorde'. The pollen parent was the unpatented *Berberis* x *media* 'Red Jewel'. The cross resulting in this new cultivar was made during Spring 2011. The new cultivar was identified as a potentially interesting selection in the Summer of 2014, at a research nursery in Mills River, North Carolina.

Asexual propagation of the new cultivar 'NCBX3' by stem cuttings was first performed during the Summer of 2014 at a research nursery in Mills River, North Carolina. Subsequent propagation has shown that the unique features of this cultivar are stable and reproduced true to type in three successive propagation cycles.

Plants of the new cultivar were first disclosed to third parties Jun. 25, 2024, in the United States. Plants were shown at an invitational event in Grand Haven, MI. This disclosure was made directly by the inventor or one who obtained the claimed invention directly or indirectly from the inventor. This and all public disclosures made between Jun. 25, 2024, and the filing of this application fall within the exception allowed under 102(b)(1).

SUMMARY OF THE INVENTION

The cultivar 'NCBX3' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NCBX3'. These characteristics in combination distinguish 'NCBX3' as a new and distinct *Berberis* cultivar:

1. Dark red, glossy foliage that develops a chartreuse margin.
2. Bright foliage color that persists all season long.
3. Low-growing, mounded habit.
4. Small spines.

PARENT COMPARISONS

Plants of the new cultivar *Berberis* 'NCBX3' are similar to plants of the seed parent in most horticultural characteristics; however, plants of the new cultivar 'NCBX3' differ in the following:

1. Foliage color of the new cultivar is dark red with a chartreuse edge, while the foliage color of the seed parent is purple without a chartreuse edge.
2. Plants of the new cultivar are larger and taller at maturity than plants of the seed parent.
3. Plants of the new cultivar have rounded, mounded habits, while plants of the seed parent have low-mounded habits.

Plants of the new cultivar *Berberis* 'NCBX3' are similar to plants of the pollen parent in most horticultural characteristics; however, plants of the new cultivar 'NCBX3' differ in the following:

1. Foliage color of the new cultivar is dark red with a chartreuse edge, while the foliage color of the pollen parent is red without a chartreuse edge.

2. Thorns of the new cultivar are smaller than thorns of the pollen parent.

COMMERCIAL COMPARISON

Plants of the new cultivar 'NCBX3' are comparable to the commercial cultivar *Berberis thunbergii* 'Crimson Pygmy', unpatented. The two *Berberis* cultivars are similar in most horticultural characteristics, however, the new cultivar 'NCBX3' differs in the following:

1. Foliage of the new cultivar develops a chartreuse margin upon maturity, while foliage of this comparator displays no variegation.
2. Foliage color of the new cultivar is a more vibrant, vivid red than the foliage color of this comparator.

BRIEF DESCRIPTION OF THE PHOTOGRAPHS

This new *Berberis* is illustrated by the accompanying photographs which show the plant's form and foliage. The colors shown are as true as can be reasonably obtained by conventional photographic procedures. Colors in the photographs may differ slightly from the color values cited in the detailed botanical description, which accurately describe the colors of the new *Berberis*.

DETAILED BOTANICAL DESCRIPTION

Figure 1:
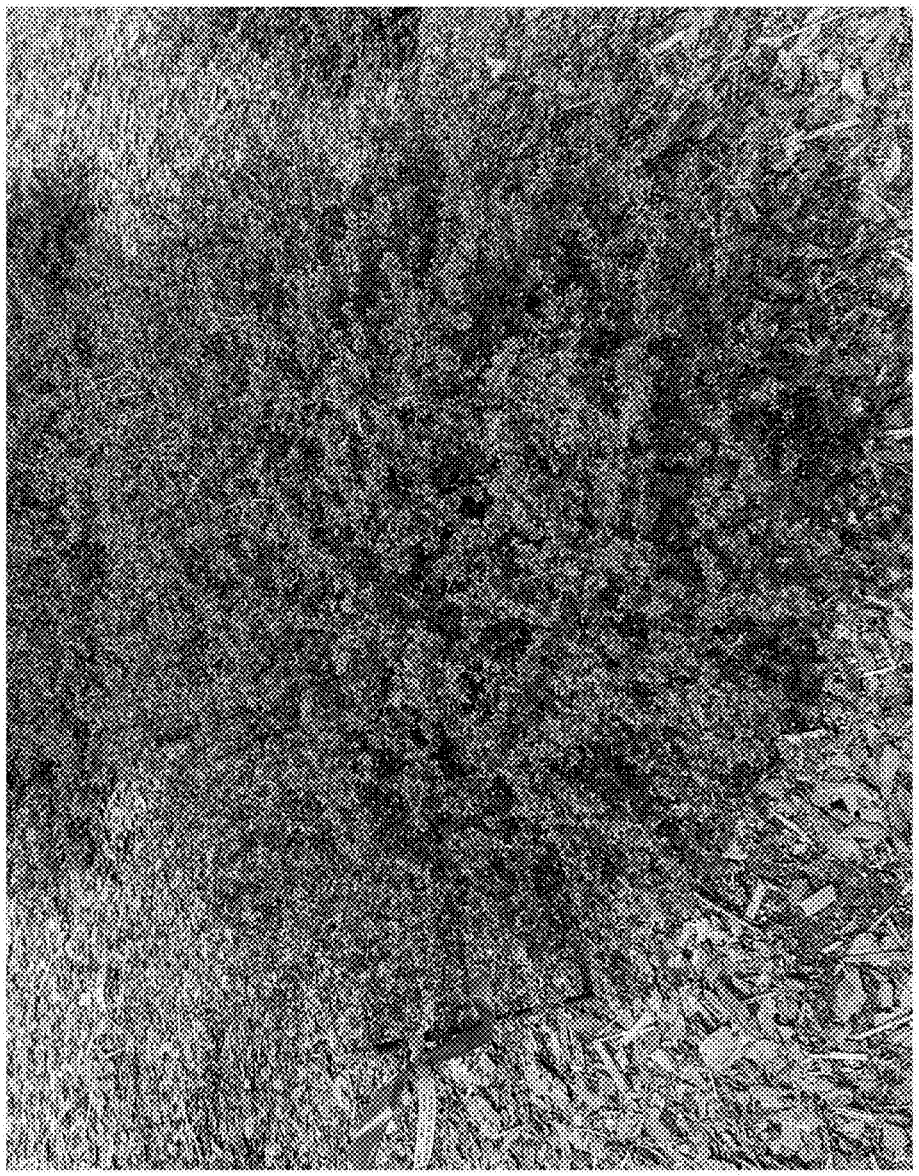
FIG. 1 is a photograph showing the habit of a ten-year-old field grown plant of 'NCBX3' in August of 2024 in Mills River, North Carolina.
Figure 2:
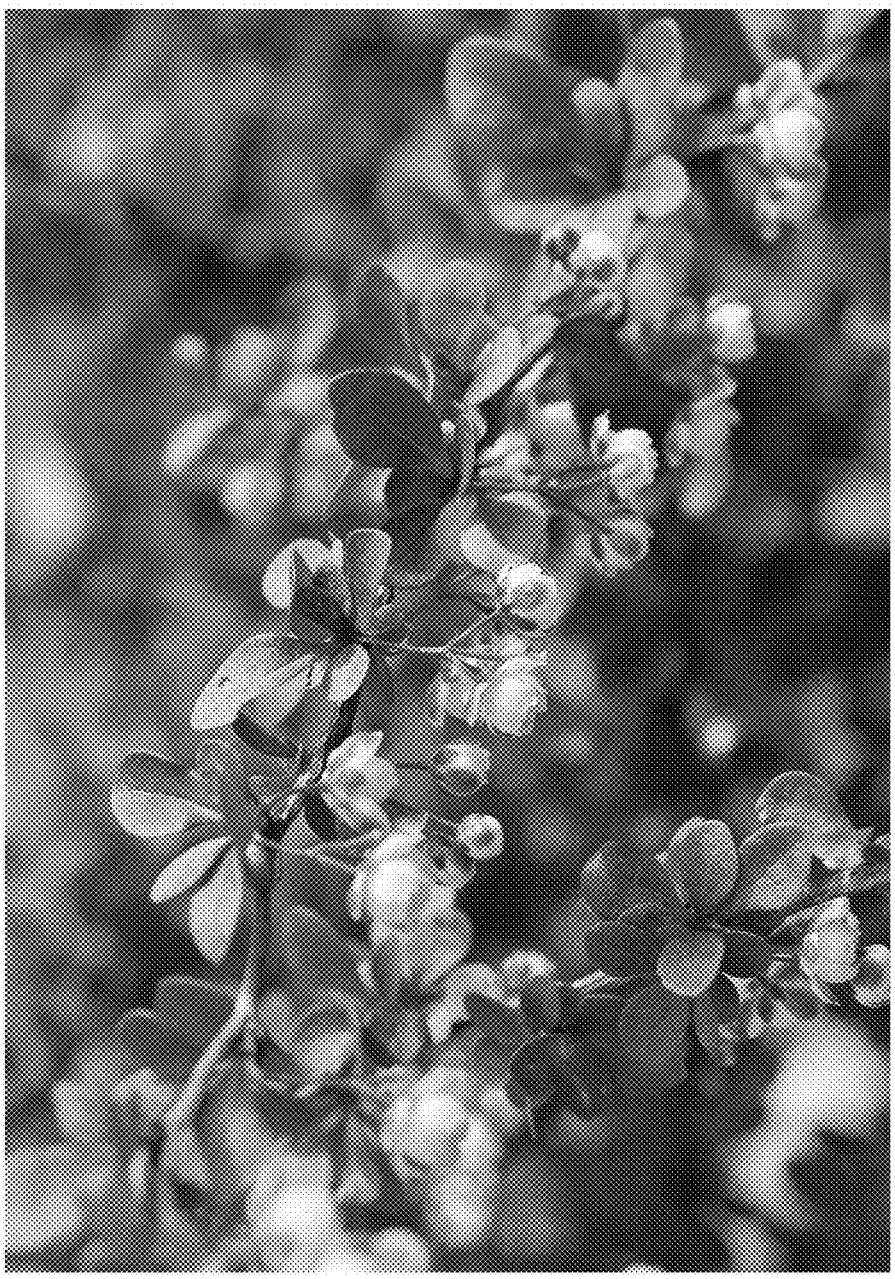
FIG. 2 is a photograph showing a close-up view of the immature foliage and flowers of 'NCBX3' on a ten-year-old field-grown plant in Spring of 2024 in Mills River, North Carolina.
Figure 3:
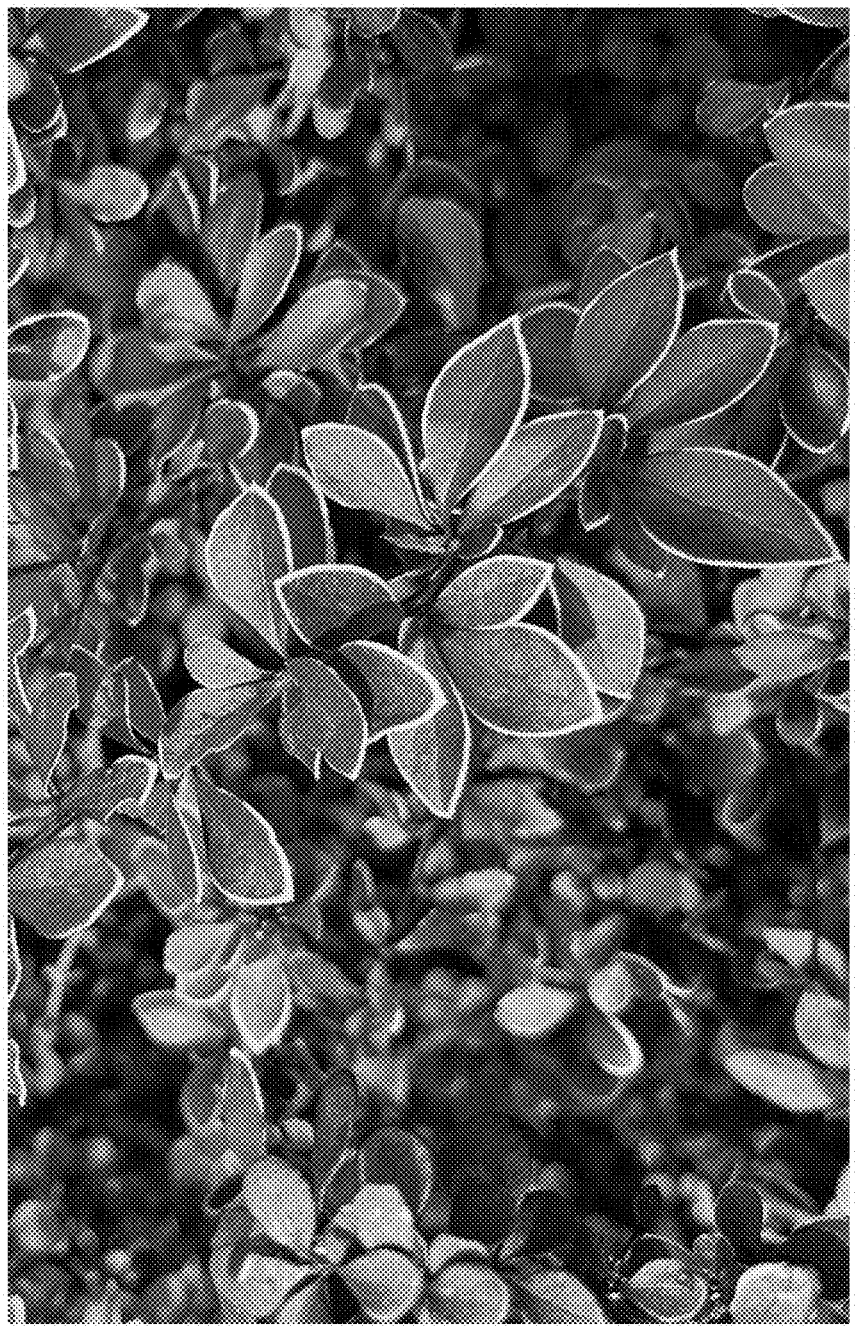
FIG. 3 is a photograph showing a close-up view of the mature foliage that has developed a chartreuse margin on a ten-year-old field-grown plant of 'NCBX3' in Mills River, North Carolina.

The following is a detailed description of the botanical characteristics of the new and distinct *Berberis* cultivar known by the denomination 'NCBX3'. The detailed description was taken on a six-year-old field-grown plant in 2020 with supplemental data taken on a ten-year-old field-grown plant in 2024 in Mills River, North Carolina. All colors cited herein refer to The Royal Horticultural Society Colour Chart (The Royal Horticultural Society (R.H.S.), London, 2015, Sixth Edition). Where specific dimensions, sizes, colors, and other characteristics are given, it is to be understood that such characteristics are approximations or averages set forth as accurately as practicable.

Botanical classification: *Berberis thunbergii* x *Berberis* x *media* 'NCBX3'.

PROPAGATION

Type of propagation typically used: Softwood cuttings.

Root description: Very thin, fibrous, not fleshy, freely branching. New roots colored near RHS Yellow-White 158D. Older roots colored near Grey-Brown 199D.

PLANT

Age of plant described: 6 and 10 years.

Plant type: Flowering shrub.

Growth habit: Densely branched and rounded.

Plant spread: 80 to 90 cm.

Plant height: 60 to 80 cm.

Stems, shoots, branches:

*Shoots* (*current year's growth*).—Shoot length: About 6 cm. Shoot diameter: About 0.1 cm. Color: RHS Red 185A. Texture: Glabrous.

*Shoots* (*prior year's growth*).—Stem length: About 7.5 cm. Stem diameter: About 0.2 cm. Color: RHS Brown 200A. Texture: Glabrous.

*Branches* (*woody branches* 2-4 *years old*).—Branch length: About 10 cm. Branch diameter: About 0.8 cm. Color: RHS Brown N200A with vertical fissures of N200C. Texture: Glabrous.

Internode length: Average 2.3 cm (1.0 to 6.5 cm).

FOLIAGE

Leaf:

*Type*.—Simple.

*Persistence*.—Deciduous.

*Arrangement*.—Alternate, whorled.

*Shape*.—Ovate to obovate.

*Length of lamina*.—Average 1.3 cm (0.9 to 1.6 cm).

*Width*.—Average 0.8 cm (0.4 to 1.3 cm).

*Apex*.—Mucronate.

*Base*.—Attenuate.

*Margin*.—Entire.

*Color, young foliage*.—Upper: RHS Red 46A. Lower: RHS Pink 182C.

*Color, mature foliage*.—Upper: RHS Red 187A with a narrow margin of Yellow-Green 150C. Lower: RHS Red-Purple N77C.

*Texture*.—Glabrous all surfaces.

*Appearance*.—Upper surface: Glossy. Lower Surface: Matte.

*Venation*.—Pinnate.

*Vein color*.—RHS Red 187A.

*Leaf attachment*.—Petiolate.

Petiole:

*Length*.—About 0.1 cm.

*Diameter*.—About 0.1 cm.

*Color*.—RHS Red 187A.

*Texture*.—Glabrous.

Spines:

*Number*.—1 per node.

*Length*.—Average 0.4 cm (0.2 to 0.5 cm).

*Width*.—Less than 0.1 cm.

*Color*.—Near RHS Brown 200B.

FLOWER

Inflorescence:

*Description*.—Umbellate fascicles occurring in the axis along the underside of branches.

*Number of flowers per inflorescence*.—1 to 5.

*Flowering season*.—Mid-April to May in Mills River, NC.

*Diameter*.—About 2 cm.

*Height*.—About 1.5 cm.

Flower:

*Shape*.—Star-shaped.

*Diameter*.—About 0.5 cm.

*Height*.—About 1.0 cm.

Bud:

*Shape*.—Rounded.

*Length*.—About 0.3 cm.

*Width*.—About 0.3 cm.
*Color*.—RHS Red 187A.

Petals:
*Number*.—5 to 6 petals.
*Arrangement*.—Whorled.
*Shape*.—Ovate.
*Length*.—About 0.4 cm.
*Width*.—About 0.3 cm.
*Margin*.—Entire.
*Apex*.—Obtuse.
*Base*.—Obtuse.
*Color*.—Upper surface: RHS Yellow 12C. Lower surface: RHS Yellow 12C.
*Texture*.—Glabrous.

Sepals:
*Number*.—5 to 6 sepals.
*Arrangement*.—Whorled.
*Shape*.—Ovate.
*Length*.—About 0.4 cm.
*Width*.—About 0.3 cm.
*Margin*.—Entire.
*Apex*.—Obtuse.
*Base*.—Obtuse.
*Color*.—RHS Yellow 8B, often with a stripe of Red 46A on the back of the sepal.
*Texture*.—Glabrous.

Peduncle:
*Length*.—Average 6.4 cm (3.2 to 9.5 cm).
*Diameter*.—About 0.1 cm.
*Color*.—Near RHS Greenish-Yellow 152C.
*Texture*.—Glabrous.

REPRODUCTIVE ORGANS

Gynoecium:
*Pistil number*.—1.
*Pistil length*.—About 0.3 cm.
*Stigma shape*.—Rounded.
*Stigma color*.—RHS Red 60A.
*Style length*.—About 0.3 cm.
*Style color*.—RHS Red 60A.

Androecium:
*Stamen number*.—6.
*Filament length*.—About 0.1 cm.
*Filament color*.—RHS Green 137B.
*Anther shape*.—Globular.
*Anther length*.—About 0.1 cm.
*Anther color*.—RHS Yellow 8A.
*Amount of pollen*.—Moderate.
*Pollen color*.—RHS Yellow 8A.

FRUIT AND SEEDS

Fruit:
*Type*.—Drupe.
*Shape*.—Ovoid.
*Length*.—About 0.6 cm.
*Width*.—About 0.2 cm.
*Color*.—RHS Red 46B.
*Texture*.—Glabrous.

Seed:
*Number per fruit*.—1 to 2.
*Shape*.—Ovoid
*Length*.—About 0.4 cm.
*Width*.—About 0.2 cm.
*Color*.—RHS Brown 200B.
*Texture*.—Glabrous, shiny.

OTHER CHARACTERISTICS

Disease/pest resistance: 'NCBX3' is documented to be resistant to Wheat Rust (*Puccinia* spp.) (Federal Register, Department of Agriculture Animal and Plant Health Inspection Service, Docket No. APHIS-2023-0050). Neither resistance nor susceptibility to other diseases and pests of *Berberis* have been observed.

Cold hardiness: At least USDA zone 6b; testing has not been completed in colder zones.

What is claimed is:

1. A new and distinct cultivar of *Berberis* plant named 'NCBX3' as herein illustrated and described.

* * * * *